US010010630B2

(12) United States Patent
Lassus et al.

(10) Patent No.: US 10,010,630 B2
(45) Date of Patent: Jul. 3, 2018

(54) GAS-FILLED MICROVESICLES

(71) Applicant: BRACCO SUISSE S.A., Manno (CH)

(72) Inventors: Anne Lassus, Carouge (CH); Philippe Bussat, Pers-Jussy (FR); Thierry Bettinger, Peillonnex (FR)

(73) Assignee: BRACCO SUISSE S.A., Manno (CH)

( * ) Notice: Subject to any disclaimer, the term of this patent is extended or adjusted under 35 U.S.C. 154(b) by 421 days.

(21) Appl. No.: 14/653,793

(22) PCT Filed: Dec. 19, 2013

(86) PCT No.: PCT/EP2013/077337
§ 371 (c)(1),
(2) Date: Jun. 18, 2015

(87) PCT Pub. No.: WO2014/096165
PCT Pub. Date: Jun. 26, 2014

(65) Prior Publication Data
US 2015/0343097 A1    Dec. 3, 2015

(30) Foreign Application Priority Data
Dec. 21, 2012   (EP) .................................... 12199095

(51) Int. Cl.
| A61K 49/22 | (2006.01) |
| A61K 9/00 | (2006.01) |
| B01J 13/02 | (2006.01) |
| A61K 49/00 | (2006.01) |
| A61K 9/127 | (2006.01) |

(52) U.S. Cl.
CPC ........ A61K 49/223 (2013.01); A61K 49/0002 (2013.01); B01J 13/02 (2013.01); *A61K 9/0019* (2013.01); *A61K 9/127* (2013.01)

(58) Field of Classification Search
CPC .............. A61K 49/223; A61K 49/0002; A61K 9/0019; A61K 9/127; B01J 13/02
See application file for complete search history.

(56) References Cited

U.S. PATENT DOCUMENTS

| 5,271,928 A | 12/1993 | Schneider et al. |
| 5,413,774 A | 5/1995 | Schneider et al. |
| 5,445,813 A | 8/1995 | Schneider et al. |
| 5,545,395 A | 8/1996 | Tournier et al. |
| 5,556,610 A | 9/1996 | Yan et al. |
| 5,597,549 A | 1/1997 | Schneider et al. |
| 5,827,504 A | 10/1998 | Yan et al. |
| 6,139,819 A | 10/2000 | Unger et al. |
| 6,258,378 B1 | 7/2001 | Schneider et al. |
| 2002/0159951 A1* | 10/2002 | Unger .................. A61K 9/1271 424/9.51 |
| 2007/0041909 A1 | 2/2007 | Kupussamy et al. |
| 2011/0268653 A1 | 11/2011 | Negrete et al. |
| 2012/0270845 A1 | 10/2012 | Bannister et al. |

FOREIGN PATENT DOCUMENTS

| EP | 0554 213 A1 | 8/1993 |
| EP | 804 251 A1 | 11/1997 |
| WO | 94/09829 A1 | 5/1994 |
| WO | 97/29783 A1 | 8/1997 |
| WO | 98/18501 A2 | 5/1998 |
| WO | 99/55383 A2 | 11/1999 |
| WO | 02/055544 A2 | 7/2002 |
| WO | 03/074005 A2 | 9/2003 |
| WO | 03/084574 A1 | 10/2003 |
| WO | 2004-037275 A1 | 5/2004 |
| WO | 2004-069284 A2 | 8/2004 |
| WO | 2005-024442 A2 | 3/2005 |
| WO | 2005/063305 A1 | 7/2005 |
| WO | 2005/063306 A1 | 7/2005 |
| WO | 2007-067979 A2 | 6/2007 |

OTHER PUBLICATIONS

Jokic et al., Czech J. Food Sci., 2013, vol. 31, , No. 2, p. 116-125. (Year: 2013).*
Database WPI Week 199517 Thomson Scientific, London GB; AN 1995-126073 XP002698969, & JP H07 48218 A (BN Yuki Noho Kenkyusho KK) Feb. 21, 1995.
European Search Report for European application No. 12199095.6, dated Jul. 1, 2013.
PCT International Search Report and Written Opinion for PCT/EP2013/077337, dated Aug. 25, 2014.
Qiu, Y. et al., "Enhancement of skin permeation of docetaxel : a novel approach combining microneedle and elastic liposomes", Journal of Controlled Release, vol. 129, n 2, 2008, pp. 144-150, XP022735035, ISSN:0168-3659, DOI:10.1016/J.JCONREL.2008.04.019.
Stevenson, K.J. et al., "The procoagulant activity of partial thromboplastin extracts : the role of phosphatidyl serine", Thrombosis Research, vol. 26, n 5, 1982, pp. 341-350, XP026453625, ISSN 0049-3848.

* cited by examiner

*Primary Examiner* — Michael G Hartley
*Assistant Examiner* — Leah H Schlientz
(74) *Attorney, Agent, or Firm* — Vivicar Law, PLLC

(57) ABSTRACT

A formulation for preparing gas-filled microvesicles which comprises a phospholipid and a mixture of saturated and unsaturated fatty acids. The gas-filled microvesicles having a stabilizing layer comprising said composition show an increased stability with respect to microvesicles containing only a saturated or an unsaturated fatty acid.

22 Claims, No Drawings

GAS-FILLED MICROVESICLES

CROSS-REFERENCE TO RELATED APPLICATIONS

This application is the national stage application of corresponding international application number PCT/EP2013/077337, filed Dec. 19, 2013, which claims priority to and the benefit of European application no. 12199095.6, filed Dec. 21, 2012, all of which are hereby incorporated by reference in their entirety.

TECHNICAL FIELD

The invention relates to new gas-filled microvesicles, to their preparation and to their use in the diagnostic and therapeutic methods.

BACKGROUND OF THE INVENTION

Rapid development of contrast agents in the recent years has generated a number of different compositions and formulations, which are useful in contrast-enhanced imaging of organs and tissue of human or animal body as well as in therapeutic treatments thereof.

A class of contrast agents, particularly useful for ultrasound contrast imaging, includes suspensions of gas bubbles of nano- and/or micro-metric size dispersed in an aqueous medium. The gas is typically entrapped or encapsulated in a stabilizing film layer comprising, for instance, emulsifiers, oils, thickeners or sugars. These stabilized gas bubbles (dispersed in a suitable physiological solution) are generally referred to in the art with various terminologies, depending typically from the stabilizing material employed for their preparation; these terms include, for instance, "microspheres", "microbubbles", "microcapsules" or "microballoons", globally referred to here as "gas-filled microvesicles" (or "microvesicles"). Of particular interest are aqueous suspensions of gas-filled microvesicles where the bubbles of gas are bounded at the gas/liquid interface by a very thin envelope (film) involving a stabilizing amphiphilic material (typically a phospholipid) disposed at the gas to liquid interface. These suspensions are advantageously prepared by contacting powdered amphiphilic materials, e.g. freeze-dried preformed liposomes or freeze-dried or spray-dried lipid solutions, with air or other gas and then with an aqueous carrier, while agitating to generate a suspension of gas-filled microvesicles which can then be administered, preferably shortly after its preparation. Examples of aqueous suspension of gas-filled microvesicles and preparation thereof are disclosed, for instance, in U.S. Pat. Nos. 5,271,928, 5,445,813, 5,413,774, 5,556,610, 5,597,549, 5,827,504, WO 97/29783 and WO2004/069284, which are herein incorporated by reference in their entirety. The stabilizing layer may comprise, in addition to the above cited phospholipids, also other amphiphilic materials, such as fatty acids. For instance, Sonovue® (an ultrasound contrast agent commercialized by Bracco Suisse S.A.) comprises a mixture of phospholipids and fatty acid as the film-forming stabilizing layer.

More recently, attention has been given to so-called "molecular imaging", where suitable target specific components are used in the formulation of the contrast agents, for allowing selective contrast-enhanced imaging of organs or tissues. In addition, therapeutic use of contrast agent formulations, optionally in combination with molecular imaging, has also been described.

The formulations of gas-filled microvesicles may be suitably modified, either for improving the diagnostic effect (e.g. through molecular imaging) and/or for therapeutic purposes, such as drug delivery and/or ultrasound mediated thrombolysis. For instance, microvesicles may be associated (e.g. by inclusion in their boundary envelope) with therapeutic agents and/or with specific components which are capable to link to a determined target within a patient's body (known as "targeting ligands"). Examples of targeting ligands include, for instance, peptides, proteins, antibodies, aptamers or carbohydrates capable of binding to specific receptors expressed by organs or tissues during pathogenic processes such as, for instance, angiogenesis, inflammation or thrombus formation.

The Applicant has now found that it is possible to improve certain characteristics of phospholipid-based gas-filled microvesicles by including in the formulation of the stabilizing layer a mixture of saturated and unsaturated fatty acids. In particular, it has been observed that the presence of said mixture of saturated/unsaturated fatty acids surprisingly increases the stability of the gas-filled microvesicle with respect to corresponding microvesicles containing only one of the respective saturated or unsaturated fatty acid in the formulation forming the stabilizing layer.

SUMMARY OF THE INVENTION

Accordingly, an aspect of the present invention relates to a suspension of gas-filled microvesicles in a physiologically acceptable liquid carrier, said microvesicles having a stabilizing envelope comprising a phospholipid, a saturated fatty acid and an unsaturated fatty acid, wherein the molar ratio between saturated and unsaturated fatty acid is from 2.5:1 to 1:8.

Preferably the molar ratio between saturated and unsaturated fatty acids is from 1.5:1 to 1:7.5, more preferably from 1:1 to 1:6, even more preferably from 1:1.5 to 1:4, particularly preferred being a molar ratio of from 1:2 to 1:3.

According to a preferred embodiment, the molar ratio between phospholipids and the mixture of saturated/unsaturated fatty acids is from 3:7 to 4:1, preferably from 2:3 to 7:3 and even more preferably from 2.5:3 to 3:2.

In a preferred embodiment, said suspension is obtained by admixing a formulation (preferably in lyophilized form) comprising phospholipids and fatty acids in the above amounts with a physiologically acceptable liquid carrier in the presence of a biocompatible gas.

Another aspect of the invention relates to a sealed vial comprising a pharmaceutical formulation and a biocompatible gas, said formulation comprising a phospholipid, a saturated fatty acid and an unsaturated fatty acid as above defined. The formulation optionally further comprises pharmaceutically acceptable additives and/or excipients. In a preferred embodiment said formulation is in a freeze-dried (lyophilized) form.

DETAILED DESCRIPTION OF THE INVENTION

The formulation of the invention comprising a mixture of saturated and unsaturated fatty acids together with a phospholipid may be used for manufacturing gas-filled microvesicles useful in diagnostic imaging and/or as therapeutic agent.

The formulation of the invention is particularly useful for forming a layer which stabilizes the bubbles of gas (stabilizing layer) in a liquid suspension. The formulation may comprise additional amphiphilic materials and is typically in the form of a freeze-dried (lyophilized) formulation, preferably comprising lyophilization additives. The gas-filled microvesicles of the invention can be prepared by admixing said formulation with a physiologically acceptable liquid carrier in the presence of a physiologically acceptable gas.

Fatty Acids

The term "fatty acids" comprises within its meanings carboxylic acids comprising a relatively long aliphatic chain, e.g. from 10 to 28 carbon atoms ($C_{10}$-$C_{28}$). The aliphatic chain is preferably a linear (straight) chain. The fatty acids useful in a composition according to the invention preferably comprise a $C_{10}$-$C_{24}$, aliphatic chain, more preferably $C_{14}$-$C_{22}$ and even more preferably a $C_{16}$-$C_{20}$ aliphatic chain terminated by a carboxylic group.

Fatty acids can be either saturated or unsaturated (i.e. containing one or more unsaturations, typically a double bond).

Saturated fatty acids comprise fatty acids with no unsaturations in the aliphatic chain such as, for instance: capric (n-decanoic), lauric (n-dodecanoic), myristic (n-tetradecanoic), palmitic (n-hexadecanoic), stearic (n-octadecanoic), arachidic (n-eicosanoic), behenic (n-docosanoic) and n-tetracosanoic acid. Preferred saturated fatty acids are myristic, palmitic, stearic and arachidic acid.

Unsaturated fatty acids may comprise one, two, three, four or five unsaturations (double bonds in particular) in the aliphatic chain. Preferably the unsaturations are in the cis-configuration. Preferably, the unsaturated fatty acid comprises three or less unsaturations, more preferably two or less unsaturations; particularly preferred are unsaturated fatty acids comprising a single unsaturation in the aliphatic chain. For the sake of brevity, unsaturated fatty acids is sometimes indicated in the following with the number of carbons of the alkyl chain and the position of the unsaturation in the chain; for instance palmitoleic acid, i.e. cis-9-hexadecenoic acid, is referred to as $C_{16}$, cis-$\Delta^9$ (or briefly: $C_{16}$, $\Delta^9$). Examples of unsaturated fatty acids comprise, for instance, decenoic, dodecenoic, tetradecenoic, hexadecenoic, hexadecadienoic, octadecenoic, octadecadienoic, octadecatrienoic, octadecatetraenoic, eicosenoic, eicosadienoic, eicosatrienoic, eicosatetraenoic, eicosapentaenoic, docosaenoic, docosadienoic, docosatrienoic, docosatetraenoic, docosapentaenoic and tetracosenoic acid. Preferred unsaturated fatty acids comprise myristoleic (cis-9-tetradecenoic), palmitoleic (cis-9-hexadecenoic), sapienic (cis-6-hexadecenoic), oleic (cis-9-octadecenoic), linoleic (cis-9, 12-octadecadienoic), linolenic (cis-9,12,15-octadecatrienoic), gondoic (cis-11-eicosenoic), cis-11,14-eicosadienoic, cis-5,8,11-eicosatrienoic, cis-8,11,14-eicosatrienoic, cis-11,14,17-eicosatrienoic, arachidonic (cis-8,11,14,17-eicosatetraenoic) and erucic (cis-13-docosenoic) acid, particularly preferred being palmitoleic, oleic and gondoic acid.

The mixture of saturated and unsaturated fatty acids preferably comprises acids having a length of the alkyl chain differing by at most four carbon atoms; more preferably the saturated and unsaturated acids differ by at most two carbon atoms and even more preferably by at most one carbon atom in their respective chain's length; particularly preferred are mixtures comprising fatty saturated and unsaturated acids having the same length of the alkyl chain (e.g. palmitic/palmitoleic acids, stearic/oleic acids, arachidic/gondonic acids, etc.).

The Applicant has observed that by using a composition comprising a molar ratio of saturated/unsaturated fatty acids of from 2.5:1 to 1:8 it is possible to prepare gas-filled microvesicles having an increased stability with respect to microvesicles where only the started or unsaturated fatty is employed in the same concentration. Preferably the molar ratio between saturated and unsaturated fatty acids in the composition is from 1.5:1 to 1:7.5, more preferably from 1:1 to 1:6, even more preferably from 1:1.5 to 1:4, particularly preferred being a molar ratio of from 1:2 to 1:3.

Phospholipids

As used herein, the term "phospholipid" is intended to encompass amphiphilic compounds containing at least one phosphate group and at least one, preferably two, ($C_{12}$-$C_{22}$) hydrocarbon chain, capable of forming a stabilizing film-layer (typically in the form of a mono-molecular layer) at the gas-water boundary interface in the final microbubbles suspension. Accordingly, these materials are also referred to in the art as "film-forming phospholipids".

The term phospholipids includes naturally occurring, semisynthetic or synthetic products, which can be employed either singularly or as mixtures.

Examples of suitable phospholipids include esters of glycerol with one or preferably two (equal or different) residues of fatty acids and with phosphoric acid, wherein the phosphoric acid residue is in turn bound to a hydrophilic group such as, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Specific examples of phospholipids are, for instance, dilauroyl-phosphatidyl-choline (DLPC), dimyristoyl-phosphatidylcholine (DMPC), dipalmitoyl-phosphatidyl-choline (DPPC), diarachidoyl-phosphatidylcholine (DAPC), distearoyl-phosphatidyl-choline (DSPC), dioleoyl-phosphatidylcholine (DOPC), 1,2 Distearoyl-sn-glycero-3-ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoylphosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleyl-phosphatidyl-choline (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidyl-glycerol (DSPG) and its alkali metal salts, dioleoyl-phosphatidylglycerol (DOPG) and its alkali metal salts, dilauroyl phosphatidic acid (DLPA), dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dilauroyl-phosphatidylethanolamine (DLPE), dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine, dilauroyl-phosphatidyl-serine (DLPS), dimyristoyl phosphatidylserine (DMPS), diarachidoyl-phosphatidyl-serine (DAPS), dipalmitoyl phosphatidylserine (DPPS), distearoylphosphatidylserine (DSPS), dioleoylphosphatidylserine (DOPS), dipalmitoyl sphingomyelin (DPSP), distearoyl-sphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Suitable phospholipids further include phospholipids modified by linking a hydrophilic polymer, such as polyethyleneglycol (PEG) or polypropyleneglycol (PPG), thereto. Preferred polymer-modified phospholipids include "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG2000 refers to DPPE having attached thereto a PEG polymer having a mean average molecular weight of about 2000.

Particularly preferred phospholipids are DAPC, DSPC, DPPC, DMPA, DPPA, DSPA, DMPG, DPPG, DSPG, DMPS, DPPS, DSPS, DPPE, DSPE, DMPE, DAPE, Ethyl-DSPC and mixtures thereof. Most preferred are DSPG, DSPS, DSPE, DSPC, DAPC and mixtures thereof. Mixtures of phospholipids can also be used, such as, for instance, mixtures of DPPE and/or DSPE (including pegylated derivates), DPPC, DSPC and/or DAPC with DSPS, DPPS, DSPA, DPPA, DSPG, DPPG, Ethyl-DSPC and/or Ethyl-DPPC.

Phospholipids the molar ratio of phospholipids with respect to the total amount of saturated or unsaturated fatty acids is from 3:7 to 4:1, preferably from 2:3 to 7:3 and even more preferably from 2.5:3 to 3:2.

Other Amphiphilic Materials

The composition forming the stabilizing layer of the gas-filled microvesicles may comprise further amphiphilic components which may also contribute to the formation of the stabilizing layer such as, for instance; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol isobutyrate, cholesterol palmitate, cholesterol stearate, lanosterol acetate, ergosterol palmitate, or phytosterol n-butyrate; sterol esters of sugar acids including cholesterol glucuronides, lanosterol glucuronides, 7-dehydrocholesterol glucuronide, ergosterol glucuronide, cholesterol gluconate, lanosterol gluconate, or ergosterol gluconate; esters of sugar acids and alcohols including lauryl glucuronide, stearoyl glucuronide, myristoyl glucuronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate; long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxy)-1-thio-β-D-mannopyranoside;;; 1,2-dioleyl-sn-glycerol; 1,2-dipalmitoyl-sn-3-succinylglycerol; 1,3-dipalmitoyl-2-succinylglycerol; palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

These further amphiphilic compounds, if present, may be present in variable amounts, for instance up to 25% by moles of the composition forming the stabilizing layer, preferably up to 10%.

Additives and Excipients

As the preparation of gas-filled microbubbles may involve a freeze drying or spray drying step, it may be advantageous to include in the formulation a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran, chitosan and its derivatives (for example: carboxymethyl chitosan, trimethyl chitosan); or a polyoxyalkyleneglycol such as polyethylene glycol. For instance, in the case of lyophilized preparation of a formulation, the amount of additive (e.g. polyethylene glycol) may vary from about 90% to about 99.99% (by weight) of the total amount of the lyophilized preparation.

Other excipients or additives may be present either in the dry formulation for the preparation of the microbubbles or may be added together with the aqueous carrier used for the reconstitution thereof, without necessarily being involved (or only partially involved) in the formation of the stabilizing envelope of the microbubble. These include pH regulators, osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars and hydrophilic polymers such as polyethylene glycol.

Targeting Ligands

Compositions and microvesicles according to the invention may optionally comprise a targeting ligand.

The term "targeting ligand" includes within its meaning any compound, moiety or residue having, or being capable to promote, a targeting activity (e.g. including a selective binding) of the microvesicles of a composition of the invention towards any biological or pathological site within a living body. Targets with which targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, and immunoglobulins and cytoplasmic receptors for steroid hormones.

The targeting ligand may be synthetic, semi-synthetic, or naturally-occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides.

The targeting ligand may be a compound per se which is admixed with the other components of the microvesicle or may be a compound which is bound to an amphiphilic molecule (typically a phospholipid) employed for the formation of the microvesicle.

In one preferred embodiment, the targeting ligand may be bound to an amphiphilic molecule (e.g. a phospholipid) forming the stabilizing envelope of the microvesicle through a covalent bond. In such a case, the specific reactive moiety that needs to be present on the amphiphilic molecule will depend on the particular targeting ligand to be coupled thereto. As an example, if the targeting ligand can be linked to the amphiphilic molecule through an amino group, suitable reactive moieties for the amphiphilic molecule may be isothiocyanate groups (that will form a thiourea bond), reactive esters (to form an amide bond), aldehyde groups (for the formation of an imine bond to be reduced to an alkylamine bond), etc.; if the targeting ligand can be linked to the amphiphilic molecule through a thiol group, suitable complementary reactive moieties for the amphiphilic molecule include haloacetyl derivatives or maleimides (to form a thioether bond); and if the targeting ligand can be linked to the amphiphilic molecule through a carboxylic group, suitable reactive moieties for the amphiphilic molecule might be amines and hydrazides (to form amide or alkylamide bonds). In order to covalently bind a desired targeting ligand, at least part of the amphiphilic compound forming the microvesicle's envelope shall thus contain a suitable reactive moiety and the targeting ligand containing the complementary functionality will be linked thereto according to known techniques, e.g. by adding it to a dispersion comprising the amphiphilic components of the microvesicle. Preferably, the amphiphilic compound is a lipid bearing a hydrophilic polymer, such as those previously mentioned, preferably a pegylated phospholipid. In this case, the targeting ligand is linked to a suitable reactive moiety on the hydrophilic polymer. The amphiphilic compound may be combined with the desired targeting ligand before preparing the microvesicle, and the so obtained combination may be used for the preparation of the microvesicle. Alternatively, the targeting ligand may be linked to the respective amphiphilic compound during the preparation of the microvesicle.

According to an alternative embodiment, the targeting ligand may also be suitably associated with the microvesicle via physical and/or electrostatic interaction. As an example, a functional moiety having a high affinity and selectivity for a complementary moiety may be introduced into the amphiphilic molecule, while the complementary moiety will be linked to the targeting ligand. For instance, an avidin (or streptavidin) moiety (having high affinity for biotin) may be covalently linked to a phospholipid (or to a pegylated phospholipid) while the complementary biotin moiety may be incorporated into a suitable targeting ligand, e.g. a peptide or an antibody. The biotin-labelled targeting ligand will thus be associated with the avidin-labelled phospholipid of the microvesicle by means of the avidin-biotin coupling system. Alternatively, both the phospholipid and the targeting ligand may be provided with a biotin moiety and subsequently coupled to each other by means of avidin (which is a bifunctional component capable of bridging the two biotin moieties). Examples of biotin/avidin coupling of phospholipids and peptides are also disclosed in the above cited U.S. Pat. No. 6,139,819. Alternatively, van der Waal's interactions, electrostatic interactions and other association processes may associate with or bind to the targeting ligand to the amphiphilic molecules.

Alternatively, the phospholipid may be modified with a protein suitable for specific coupling to Fc domain of Immunoglubulin (Ig) such as Protein A, Protein G, Protein A/G or Protein L. According to an alternative embodiment, the targeting ligand may be a compound which is admixed with the components forming the microvesicle, to be eventually incorporated the microvesicle structure, such as, for instance, a lipopeptide as disclosed e.g. in International patent Applications WO 98/18501 or 99/55383, both herein incorporated by reference.

Alternatively, a microvesicle may first be manufactured, which comprises a compound (lipid or polymer-modified lipid) having a suitable moiety capable of interacting with a corresponding complementary moiety of a targeting ligand; thereafter, the desired targeting ligand is added to the microvesicle suspension, to bind to the corresponding complementary moiety on the microvesicle.

Examples of suitable specific targets to which the microvesicles may be directed are, for instance, fibrin and the GPIIbIIIa binding receptor on activated platelets. Fibrin and platelets are in fact generally present in "thrombi", i.e. coagula which may form in the blood stream and cause a vascular obstruction. Suitable binding peptides are disclosed, for instance, in the above cited U.S. Pat. No. 6,139,819. Further binding peptides specific for fibrin-targeting are disclosed, for instance, in International patent application WO 02/055544, which is herein incorporated by reference.

Other examples of important targets include receptors in vulnerable plaques and tumor specific receptors, such as kinase domain region (KDR) and VEGF (vascular endothelial growth factor)/KDR complex. Binding peptides suitable for KDR or VEGF/KDR complex are disclosed, for instance, in International Patent application WO 03/74005 and WO 03/084574, both herein incorporated by reference.

Preparation of Microvesicles

The microvesicles according to the invention may be manufactured from the composition of the invention according to any known method in the art. Typically, the manufacturing method involves the preparation of a dried powdered material comprising the composition of the invention, preferably by lyophilization (freeze drying) of an aqueous or organic suspension comprising said composition. The microvesicles may then be obtained by reconstitution of the lyophilized preparation in an aqueous carrier, upon gentle agitation in the presence of a gas.

Preferably, as disclosed for instance in International patent application WO2004/069284, a composition comprising the mixture of phospholipids and fatty acids may be dispersed in an emulsion of water with a water immiscible organic solvent (e.g. branched or linear alkanes, alkenes, cyclo-alkanes, aromatic hydrocarbons, alkyl ethers, ketones, halogenated hydrocarbons, perfluorinated hydrocarbons or mixtures thereof) under agitation, preferably in admixture with a lyoprotecting agent (such as those previously listed, in particular carbohydrates, sugar alcohols, polyglycols, polyoxyalkylene glycols and mixtures thereof). The emulsion may be obtained by submitting the aqueous medium and the solvent in the presence of the phospholipids and fatty acids to any appropriate emulsion-generating technique known in the art, such as, for instance, sonication, shaking, high pressure homogenization, micromixing, membrane emulsification, high speed stirring or high shear mixing. The so obtained microemulsion, which contains microdroplets of solvent surrounded and stabilized by phospholipids and fatty acids (and optionally by other amphiphilic film-forming compounds and/or additives), is then lyophilized according to conventional techniques to obtain a lyophilized material.

The dried or lyophilized product is generally in the form of a powder or a cake, and may be stored (typically in a vial) in contact with the desired gas. The product is readily reconstitutable in a suitable physiologically acceptable aqueous liquid carrier, which is typically injectable, to form a suspension of gas-filled microbubbles, upon gentle agitation of the suspension in the presence of a biocompatible gas. Suitable physiologically acceptable liquid carriers are sterile water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (e.g. glucose, sucrose, sorbitol, mannitol, glycerol, polyethylene glycols, propylene glycols and the like), chitosan derivatives, such as carboxymethyl chitosan, trimethyl chitosan or gelifying compounds, such as carboxymethylcellulose, hydroxyethyl starch or dextran.

Gas

Any biocompatible gas, gas precursor or mixture thereof may be employed to form the microvesicles of the invention (hereinafter also identified as "microvesicle-forming gas"). The term "biocompatible gas" (or gas precursor) includes any gas (or precursor thereof) which at the usual dosages of the relevant diagnostic or therapeutic application does not result in any significant adverse or toxic effect to a patient.

The gas may comprise, for example, air; nitrogen; oxygen; carbon dioxide; hydrogen; nitrous oxide; nitric oxide; a noble or inert gas such as helium, argon, xenon or krypton; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{12}$.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures may be found, for instance, in WO 94/09829, which is herein incorporated by reference. The following combinations are particularly preferred: a mixture of gases (A) and (B) in which the gas (B) is a fluorinated gas, selected among those previously illustrated, including mixtures thereof, and (A) is selected from air, oxygen, nitrogen, carbon dioxide or mixtures thereof.

The amount of gas (B) may represent from about 0.5% to about 95% v/v of the total mixture, preferably from about 5% to 80%.

Particularly preferred gases are $SF_6$, $C_3F_8$, $C_4F_{10}$ or mixtures thereof, optionally in admixture with air, oxygen, nitrogen, carbon dioxide or mixtures thereof.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

Agents or Components Associated with the Microvesicles

The microvesicles according to the invention may optionally further comprise a diagnostic agent and/or a therapeutic agent, either included into the microvesicle structure or associated therewith.

The term "diagnostic agent" includes within its meaning any compound, composition or particle which may be used in connection with methods for imaging an internal region of a patient and/or diagnosing the presence or absence of a disease in a patient. In particular, diagnostic agents incorporated into or associated with a microvesicle in a composition of the invention are any compound, composition or particle which may allow imaging enhancement in connection with diagnostic techniques, including, magnetic resonance imaging, X-ray, in particular computed tomography, optical imaging, nuclear imaging or molecular imaging. Examples of suitable diagnostic agents are, for instance, magnetite nanoparticles, iodinated compounds, such as Iomeprol®, or paramagnetic ion complexes, such as hydrophobic gadolinium complexes.

The term "therapeutic agent" includes within its meaning any substance, composition or particle which may be used in any therapeutic application, such as in methods for the treatment (including diagnosis, prevention, alleviation, pain relief or cure) of a disease in a patient, as well as any substance which is capable of exerting or is responsible to exert a biological effect in vitro and/or in vivo. Therapeutic agents thus include any compound or material capable of being used in the treatment of any pathological status in a patient (including malady, affliction, disease lesion or injury) as well as in the prevention of any such pathological status (e.g. vaccination). Examples of therapeutic agents are drugs, pharmaceuticals, bioactive agents, cytotoxic agents, chemotherapy agents, radiotherapeutic agents, proteins, natural or synthetic peptides, including oligopeptides and polypeptides, vitamins, steroids and genetic material, including nucleosides, nucleotides, oligonucleotides, polynucleotides and plasmids.

The microvesicles of the invention may also be associated with other components such as, for instance, liposomes or micelles. Said components may simply be admixed together with the microvesicles or may form an assembly through a physical and/or chemical interaction with the stabilizing envelope of the microvesicles, e.g through a covalent bound, an electrostatic or ionic interaction, Van der Waals interaction, hydrophobic or hydrophilic interaction. Examples of these associated microvesicles compositions and of the preparation thereof are disclosed, for instance, in U.S. Pat. No. 6,258,378 and in International Patent Applications WO2005/063305 and WO2005/063306, all herein incorporated by reference. These components associable or associated with the microvesicles may in turn bear any of the above listed targeting ligands, diagnostic agents or therapeutic agents, which will thus be associated with the microvesicles through said component. For instance, magnetite nanoparticles may be admixed with a charged amphiphilic material, such as those previously mentioned, in order to stabilize said particles and keep them dispersed in an aqueous solution (as disclosed for instance in U.S. Pat. No. 5,545,395, herein incorporated by reference), in order to associate it with a microvesicle. Alternatively, gadolinium complexes may be admixed with suitable micelle-forming compounds, for instance as disclosed in European Patent EP 804 251 (herein incorporated by reference), and the formed micelle may be associated with a microvesicle. Similarly, a therapeutic agent may be prepared as a micellar or liposomal suspension and as such being associated with a microvesicle.

Pharmaceutical Kit and Administration

The microvesicles according to the invention are preferably stored in dried powdered form and as such may advantageously be packaged in a two component diagnostic and/or therapeutic kit, preferably for administration by injection. The kit preferably comprises a first container, containing the lyophilized composition in contact with a selected biocompatible gas and a second container, containing a physiologically acceptable aqueous carrier. Examples of suitable carriers are water, typically sterile, pyrogen free water (to prevent as much as possible contamination in the intermediate lyophilized product), aqueous solutions such as saline (which may advantageously be balanced so that the final product for injection is not hypotonic), or aqueous solutions of one or more tonicity adjusting substances such as salts or sugars, sugar alcohols, glycols or other non-ionic polyol materials (e.g. glucose, sucrose, sorbitol, mannitol, glycerol, polyethylene glycols, propylene glycols and the like). Said two component kit may include two separate containers or a dual-chamber container. In the former case the container is preferably a conventional septum-sealed vial, wherein the vial containing the lyophilized residue is sealed with a septum through which the carrier liquid may be injected using an optionally prefilled syringe. In such a case the syringe used as the container of the second component is also used then for injecting the contrast agent. In the latter case, the dual-chamber container is preferably a dual-chamber syringe and once the lyophilisate has been reconstituted and then suitably mixed or gently shaken, the container can be used directly for injecting the contrast agent.

The microvesicles of the present invention may be used in a variety of diagnostic and/or therapeutic techniques, including in particular Ultrasound and Magnetic Resonance.

Diagnostic techniques include any method where the use of the gas-filled microvesicles allows enhancing the visualisation of a portion or of a part of an animal (including humans) body, including imaging for preclinical and clinical research purposes. A variety of imaging techniques may be employed in ultrasound applications, for example including fundamental and harmonic B-mode imaging, pulse or phase inversion imaging and fundamental and harmonic Doppler imaging; if desired three-dimensional imaging techniques may be used.

Microvesicles according to the invention may typically be administered in a concentration of from about 0.01 to about 1.0 μL of gas per kg of patient, depending e.g. on their respective composition, the tissue or organ to be imaged and/or the chosen imaging technique. This general concentration range may of course vary depending on specific imaging applications, e.g. when signals can be observed at very low doses such as in colour Doppler or power pulse inversion.

Possible other diagnostic imaging applications include scintigraphy, light imaging, and X-ray imaging, including X-ray phase contrast imaging.

Therapeutic techniques include any method of treatment (as above defined) of a patient which comprises the use of gas-filled microvesicles either as such (e.g. ultrasound mediated thrombolysis) or in combination with a therapeutic agent (e.g. for the delivery of a bioactive compound to a selected site or tissue, such as in gene therapy or in the use as vaccine), and which is capable of exerting or responsible to exert a biological effect in vitro and/or in vivo, either by itself or upon specific activation by various physical methods (including e.g. ultrasound mediated delivery).

Microvesicles according to the invention can typically be administered in a concentration of from about 0.01 to about 5.0 μL of gas per kg of patient, depending e.g. from their respective composition, the type of subject under treatment, the tissue or organ to be treated and/or the therapeutic method applied.

The following examples will help to further illustrate the invention.

EXAMPLES

Materials

| | |
|---|---|
| DPPC | Dipalmitoylphosphatidylcholine (Genzyme) IUPAC: 1,2-Dipalmitoyl-sn-glycero-3-phosphocholine |
| DSPC | Distearoylphosphatidylcholine (Sygena) IUPAC: 1,2-Distearoyl-sn-glycero-3-phosphocholine |
| DAPC | Diarachidoylphosphatidylcholine (Genzyme) IUPAC: 1,2-Diarachidoyl-sn-glycero-3-phosphocholine |
| DSPG | Distearoylphosphatidylglycerol sodium salt (Genzyme) IUPAC: 1,2-Distearoyl-sn-glycero-3-[phospho-rac-(1-glycerol)] |
| DSPS | Distearoylphosphatidylserine (Genzyme) IUPAC: 1,2-distearoyl-sn-glycero-3-phospho-L-serine (sodium salt) |
| DSPE-PEG2000 | Distearoyl phosphoethanolamine polyethylene glycol 2000, ammonium salt (Genzyme) IUPAC: 1,2-distearoyl-sn-glycero-3-phosphoethanolamine-N-[methoxy(polyethylene glycol)-2000] |
| Fatty acids | Supplied by Sigma |
| PEG4000 | Polyethyleneglycol, MW = 4000 (Fluka) |
| $C_4F_{10}$ | Perfluorobutane (from F2 chemicals) |
| Culture Medium | RPMI 1640 (Sigma R0883) supplemented with 10% Fetal bovine serum (A15-101 from PAA), Penicillin-streptomycin, HEPES, L-glutamine, non-essential amino acids and Na-pyruvate |

Dimensions and concentration of microvesicles are determined by Coulter counter Multisizer3 (aperture: 30 μm).

The numbering in the preparation in the following examples identifies the various combinations of phospholipids with the acronym NxXn, where:

N is a number identifying whether the composition contains only a saturated fatty acid (1), only an unsaturated fatty acid (2) or a mixture of the two (3 or higher, where numbers higher than 3 identify different molar ratios between the two fatty acids)

x is a letter identifying the fatty acid's chain length (a=$C_{16}$; b, b', b''=$C_{18}$; c, c'=$C_{20}$; where b' (and c') and b'' identify unsaturated fatty acids with two or three unsaturations, respectively);

X is a letter (capital) identifying the type of phospholipid (A=DSPC, B=DSPG, C=DSPS, D=DPPC and E=DAPC); and n is another number identifying similar relative molar amounts of the phospholipid in the different preparations.

For instance, 3b'A1 identifies a mixture 1/2.5 by moles (N=3) of $C_{18}$ fatty acids (b), the unsaturated acid containing two unsaturations (x=b'), with DSPC (X=A) in a relative amount of 52% by moles (n=1); similarly, 3aC1 identifies a mixture 1/2.5 by moles (N=3) of $C_{16}$ fatty acids (x=a), with DSPS (X=C) in a relative amount of 52% by moles (n=1).

Example 1 (Comparative)

Preparation of Microvesicles Containing Saturated or Unsaturated Fatty Acid 15.6 mg of DSPC (52% by moles) and 4.4 mg of palmitic acid (45.5% by moles) were admixed in THF, evaporated at 60° C. and dried overnight at 25° C. under vacuum (0.2 mbar); the residue was dissolved in cyclooctane (1.6 mL) at 70° C. until a clear, homogeneous solution was obtained.

DSPE-PEG2000 (2.6 mg) was mixed with 200 μL of distilled water. After heating (50° C.) and mixing, a clear micellar solution is obtained and added to 20 mL of a solution of PEG 4000 at 10% (w/v) in distilled water.

The organic phase is added in the aqueous phase under stirring with high speed homogenizer Polytron (1 min at 9'000 rpm). The obtained emulsion was left one hour at 80° C. under gentle stirring and cooled down to room temperature. The emulsion was diluted twice with a solution of PEG 4000 10% (w/v), and aliquoted in DIN4R vials (0.5 mL of emulsion per vial). The emulsion in the vials was lyophilized and a mixture of $C_4F_{10}$/air (35%-65%) was introduced into the vial. Vials were frozen at −50° C. for 1 h (Telstar lyophilizer), then freeze-dried at −25° C. and 0.2 mbar for 12 h. The content of the vial was then redispersed in NaCl 0.9% (1 mL) under gentle agitation to give the suspension of gas-filled microvesicles.

The above preparation was repeated by replacing palmitic acid with similar molar amount of other saturated and unsaturated fatty acids, as indicated in the following table 1.

TABLE 1

Microvesicles comprising saturated or unsaturated fatty acids

| Preparation | DSPC (mg) | Type of Fatty acid | Amount of F. Ac. (mg) | Microv. Conc. (part./mL) |
|---|---|---|---|---|
| 1aA1 | 15.6 | Palmitic ($C_{16}$) | 4.4 | $2.9 \times 10^9$ |
| 2aA1 | 15.6 | Palmitoleic ($C_{16}$, $\Delta^9$) | 4.4 | $2.1 \times 10^9$ |
| 1bA1 | 15.2 | Stearic ($C_{18}$) | 4.8 | $2.4 \times 10^9$ |
| 2bA1 | 15.2 | Oleic ($C_{18}$, $\Delta^9$) | 4.8 | $2.1 \times 10^9$ |
| 2b'A1 | 15.1 | Linoleic ($C_{18}$, $\Delta^{9,12}$) | 4.9 | $2.0 \times 10^9$ |
| 2b''A1 | 15.3 | Linolenic ($C_{18}$, $\Delta^{9,12,15}$) | 4.7 | $1.5 \times 10^9$ |
| 1cA1 | 14.9 | Arachidic ($C_{20}$) | 5.1 | $3.4 \times 10^9$ |
| 2cA1 | 14.9 | Eicosenoic ($C_{20}$, $\Delta^{11}$) | 5.1 | $2.7 \times 10^9$ |
| 2c'A1 | 14.9 | Eicosadienoic ($C_{20}$, $\Delta^{11,14}$) | 5.1 | $1.7 \times 10^9$ |

Example 2

Microvesicles Containing Mixtures of Saturated and Unsaturated Fatty Acids

Preparation 1a of Example 1 was repeated by replacing the palmitic acid with the similar molar amount (about 45.5%) of a mixture containing a saturated fatty acid (about 13% by moles; 1.5 to 1.8 mg) and unsaturated fatty acid (about 32.5% by moles 3.7 to 4.4 mg), as indicated in the following table 2, admixed with 18.2 to 18.5 mg of DSPC (total to 20 mg with amount of saturated acid) and 3.0 mg of DSPE-PEG2000.

TABLE 2

Microvesicles with mixtures of saturated/unsaturated fatty acids

| Preparation | Sat. fatty acid (mg) | Unsat. fatty acid (mg) | Micr. Conc. (part./mL) |
|---|---|---|---|
| 3aA1 | Palmitic - 1.5 | Palmitoleic - 3.7 | $2.9 \times 10^9$ |
| 3bA1 | Stearic - 1.7 | Oleic - 4.1 | $3.2 \times 10^9$ |
| 3b'A1 | Stearic - 1.7 | Linoleic - 4.1 | $2.9 \times 10^9$ |
| 3b"A1 | Stearic - 1.7 | Linolenic - 4.0 | $2.8 \times 10^9$ |
| 3cA1 | Arachidic - 1.8 | Eicosenoic - 4.5 | $3.3 \times 10^9$ |
| 3c'A1 | Arachidic - 1.8 | Eicosadienoic - 4.4 | $3.7 \times 10^9$ |
| 3ab'A1 | Palmitic - 1.5 | Linoleic - 4.1 | $3.2 \times 10^9$ |
| 3ab"A1 | Palmitic - 1.5 | Linolenic - 4.1 | $2.6 \times 10^9$ |

Example 3

Stability of Microvesicles Comprising Mixtures of Saturated/Unsaturated Fatty Acids Compared with Microvesicles Comprising Saturated or Unsaturated Fatty Acids The stability of the microvesicles prepared in Examples 1 and 2 was measured in the above identified Culture Medium at 37° C. over 24 hours. Two vials of each preparation were redispersed in 1 mL of Culture Medium and samples were characterized by Coulter Counter i) right after reconstitution and ii) after 24 hours of incubation at 37° C. under static condition. The percentage of remaining microvesicles (with respect to the initial amount measured after reconstitution) is reported in the following table 3.

TABLE 3

Stability of microvesicles

| Preparation | Saturated fatty acid | Mixture of saturated/unsaturated fatty acids | Unsaturated fatty acid | Stability (% after 24 h) |
|---|---|---|---|---|
| 1aA1* | Palmitic | | | 32 |
| 2aA1* | | | Palmitoleic | 31 |
| 3aA1 | | Palmitic/Palmitoleic | | 86 |
| 1bA1* | Stearic | | | 22 |
| 2bA1* | | | Oleic | 70 |
| 3bA1 | | Stearic/Oleic | | 77 |
| 2b'A1* | | | Linoleic | 43 |
| 3b'A1 | | Stearic/Linoleic | | 85 |
| 3ab'A1 | | Palmitic/Linoleic | | 74 |
| 2b"A1* | | | Linolenic | 19 |
| 3b"A1 | | Stearic/Linolenic | | 63 |
| 3ab"A1 | | Palmitic/Linolenic | | 62 |
| 1c*A1 | Arachidic | | | 55 |
| 2c*A1 | | | Eicosenoic | 51 |
| 3cA1 | | Arachidic/Eicosenoic | | 81 |
| 2c'*A1 | | | Eicosadienoic | 35 |
| 3c'A1 | | Arachidic/Eicosadienoic | | 90 |

*= comparative

As inferable from the above table, mixtures of saturated and unsaturated fatty acids (molar ratio of about 1:2.5) provide increased stability of microvesicles with respect to microvesicles containing the same molar amount of only the saturated or of the unsaturated fatty acid.

Example 4

Preparation and Stability Measures of Microvesicles with Various Molar Ratios of Arachidic Acid Over Eicosenoic Acid Preparation 3c of Example 2 was repeated but the molar ratio of the saturated fatty acid over the unsaturated fatty acid was varied as illustrated in table 4 (while keeping the total molar amount of saturated+unsaturated fatty acids constant at about 45.5% molar), the remainder components being DSPC (52% molar) and DSPE-PEG2000 (2.5% molar).

The stability in culture medium of the obtained microvesicles was determined as illustrated above and compared with the one of microbubbles with only arachidic acid or eicosenoic acid (preparations 1c and 2c, total amount of each fatty acid about 45.5% molar). Results are reported in table 4 below

TABLE 4

Stability of microvesicles containing mixtures of arachidic acid and eicosenoic acid

| Preparation | Arachidic Acid (mg) | Eicosenoic acid (mg) | Molar ratio | Micr. Conc. (part./mL) | Stability (% after 24 h) |
|---|---|---|---|---|---|
| 1c*A1 | 5.1 | 0 | — | $3.4 \times 10^9$ | 55 |
| 4cA1 | 4.7 | 0.6 | 7.3/1 | $2.9 \times 10^9$ | 55 |
| 5cA1 | 4.0 | 1.6 | 2.5/1 | $2.9 \times 10^9$ | 65 |
| 6cA1 | 2.9 | 2.9 | 1/1 | $3.0 \times 10^9$ | 64 |
| 3cA1 | 1.8 | 4.5 | 1/2.5 | $3.3 \times 10^9$ | 81 |
| 7cA1 | 0.8 | 5.8 | 1/7.3 | $3.4 \times 10^9$ | 59 |
| 2c*A1 | 0 | 5.1 | — | $2.7 \times 10^9$ | 51 |

*= comparative

As inferable from the above table, an increased stability is observed for microbubbles comprising a mixture of saturated/unsaturated fatty acids of from 2.5/1 to 1/7.3 molar.

Example 5

Preparation and Stability Measures of Microvesicles with Various Molar Ratios of Palmitic Acid Over Palmitoleic Acid Preparation 3a of Example 2 was repeated but the molar ratio of the saturated fatty acid over the unsaturated fatty acid was varied as illustrated in table 5 (while keeping the total molar amount of saturated+unsaturated fatty acids constant at about 45.5% molar), the remainder components being DSPC (52% molar) and DSPE-PEG2000 (2.5% molar).

The stability in culture medium of the obtained microvesicles was determined as illustrated above and compared with the one of microbubbles with only palmitic acid or palmitoleic acid (preparations 1a and 2a, total amount of each fatty acid about 45.5% molar). Results are reported in table 5 below.

TABLE 5

Microvesicles with different ratios of palmitic/palmitoleic acids

| Preparation | Palmitic acid (mg) | Palmitoleic acid (mg) | Molar Ratio | (part./mL) | Stability (% after 24 h) |
|---|---|---|---|---|---|
| 1a*A1 | 4.4 | 0 | — | $2.9 \times 10^9$ | 32.5 |
| 4aA1 | 4.0 | 0.5 | 7.3/1 | $2.7 \times 10^9$ | 33 |
| 5aA1 | 2.9 | 1.9 | 1.5/1 | $2.4 \times 10^9$ | 50 |
| 6aA1 | 2.5 | 2.5 | 1/1 | $3.0 \times 10^9$ | 48 |
| 3aA1 | 1.5 | 3.7 | 1/2.5 | $2.9 \times 10^9$ | 86 |
| 7aA1 | 0.7 | 4.8 | 1/7.3 | $2.6 \times 10^9$ | 58 |
| 2a*A1 | 0 | 4.4 | — | $2.1 \times 10^9$ | 31 |

*= comparative

As inferable from the above table, an increased stability is observed for microbubbles comprising a mixture of saturated/unsaturated fatty acids of from 1.5/1 to 1/7.3 molar.

Example 6

Microvesicles with Mixture of Saturated/Unsaturated Fatty Acids and Varying Amounts of Phosphatidylcholine Preparation 3a of Example 2 was repeated but the molar amount of DSPC was varied with respect to the molar amount of the fatty acid mixture, as illustrated in table 6 below (the molar ratio saturated/unsaturated fatty acids being kept constant at 1:2.5). The total number of moles (DSPC+palmitic acid+palmitoleic acid) for each preparation was kept constant at about 45 μmoles.

The stability in culture medium of the obtained microvesicles was determined as illustrated above and the results are reported in table 6 below.

TABLE 6

Stability of microvesicles containing different molar ratios of phospholipids vs. mixture saturated/unsaturated fatty acids

| Preparation | DSPC (mg) | Molar ratio DSPC/fatty acids | Concentration (part./mL) | Stability (% after 24 h) |
|---|---|---|---|---|
| 3a* | 0 | — | $0.2 \times 10^9$ | 30 |
| 3aA2 | 8.9 | 1/2.9 | $1.7 \times 10^9$ | 47 |
| 3aA3 | 11.6 | 1/2 | $2.4 \times 10^9$ | 66 |
| 3aA1 | 18.5 | 1.1/1 | $2.9 \times 10^9$ | 86 |
| 3aA4 | 23.1 | 2/1 | $3.1 \times 10^9$ | 52 |
| 3aA5 | 26.7 | 3.3/1 | $3.6 \times 10^9$ | 30 |
| A0* | 34.7 | — | $2.9 \times 10^9$ | 33 |

*= comparative

As inferable from the above table, when the molar amount of phospholipids with respect to the mixture of saturated and unsaturated fatty acids is from about 1/3 to about 2/1, the microvesicles have an increased stability.

Example 7

Microvesicles Comprising Phosphatidylglycerol Combined with Mixture of Saturated/Unsaturated Fatty Acids Preparations 1a, 2a (Example 1) and 3a (Example 2) were repeated but phosphatidylcholine (DSPC) was replaced by phosphatidylglycerol (DSPG). The stability of the obtained microvesicles was determined as above described and the results are reported in the following table 7 below.

TABLE 7

Stability of microvesicles containing DSPG

| Preparation | Palmitic acid (% mol) | Palmitoleic acid (% mol) | Microvesicles concentration (part./mL) | Stability (% after 24 h) |
|---|---|---|---|---|
| 1aB1* | 45 | | $2.2 \times 10^9$ | 16 |
| 2aB1* | | 45 | $2.3 \times 10^9$ | 19 |
| 3aB1 | 13 | 32.5 | $2.7 \times 10^9$ | 54 |

*= comparative

As inferable from the above table, mixtures of saturated/unsaturated fatty acids provide increased stability also to phosphatidylglycerol-containing microvesicles, when compared to compositions containing the same molar amount of only the saturated or unsaturated fatty acid.

Example 8

Microvesicles Comprising Phosphatidylserine Combined with Mixture of Saturated/Unsaturated Fatty Acids Example 7 was repeated but the phosphatidylglycerol (DSPG) was replaced by phosphatidylserine (DSPS). The stability of the obtained microvesicles was determined as above described and the results are reported in the following table 8 below.

TABLE 8

Stability of microvesicles containing DSPS

| Preparation | Palmitic acid (% mol) | Palmitoleic acid (% mol) | Microvesicles (part./mL) | Stability (% after 24 h) |
|---|---|---|---|---|
| 1aC1* | 45 | | $2.2 \times 10^9$ | 37 |
| 2aC1* | | 45 | $1.7 \times 10^9$ | 39 |
| 3aC1 | 13 | 32.5 | $2.5 \times 10^9$ | 50 |

*= comparative

As inferable from the above table, mixtures of saturated/unsaturated fatty acids provide increased stability also to phosphatidylserine-containing microvesicles, when compared to the composition containing the same molar amount of only the saturated or unsaturated fatty acid.

Example 9

Microvesicles Comprising Phosphatidylcholine Combined with Mixture of Saturated/Unsaturated Fatty Acids Example 7 was repeated but the phosphatidylglycerol (DSPG) was replaced by phosphatidylcholine (DPPC) and the fatty acids were replaced by stearic acid and oleic acid. The stability of the obtained microvesicles was determined as above described and the results are reported in the following table 9 below.

TABLE 9

Stability of microvesicles containing DPPC

| Preparation | Stearic acid (% mol) | Oleic acid (% mol) | Microvesicles (part./mL) | Stability (% after 24 h) |
|---|---|---|---|---|
| 1bD1* | 45 | | $3.2 \times 10^9$ | 6 |
| 2bD1* | | 45 | $2.4 \times 10^9$ | 6 |
| 3bD1 | 13 | 32.5 | $2.3 \times 10^9$ | 30 |

*= comparative

As inferable from the above table, mixtures of saturated/unsaturated fatty acids provide increased stability also to phosphatidylcholine-containing microvesicles, when compared to the composition containing the same molar amount of only the saturated or unsaturated fatty acid.

Example 10

Microvesicles Comprising Phosphatidylcholine Combined with Mixture of Saturated/Unsaturated Fatty Acids Example 9 was repeated but DPPC was replaced by DAPC. The stability of the obtained microvesicles was determined as above described and the results are reported in the following table 10 below.

TABLE 10

Stability of microvesicles containing DAPC

| Preparation | Stearic acid (% mol) | Oleic acid (% mol) | Microvesicles (part./mL) | Stability (% after 24 h) |
|---|---|---|---|---|
| 1bE1* | 45 | | $1.5 \times 10^9$ | 62 |
| 2bE1* | | 45 | $1.6 \times 10^9$ | 45 |
| 3bE1 | 13 | 32.5 | $2.7 \times 10^9$ | 90 |

*= comparative

The above data confirm that mixtures of saturated/unsaturated fatty acids provide increased stability to microvesicles containing phosphatidylcholine (with a different fatty acid chain), when compared to the composition containing the same molar amount of only the saturated or unsaturated fatty acid.

Example 11

In-vivo Ultrasound Imaging of Microvesicles Comprising Mixtures of Saturated and Unsaturated Fatty Acids Gas-filled microvesicles prepared according to preparation 1aA1 (DSPC and palmitic acid–PA) were compared with microvesicles prepared according to preparation 3aA1 (DSPC+mixture of palmitic and palmitoleic acids–PA/POA), for their respective perfusion performances in vivo (rat kidney).

The respective perfusion performance of the microvesicle preparations was evaluated by ultrasound imaging performed using a Siemens Sequoia 512 scanner (Siemens Medical Systems, Issaquah, Wash.) equipped with a 15L8 linear transducer. Intermittent muscle imaging was performed using Cadence Pulse Sequencing (CPS) mode at low acoustic power (MI 0.25) to follow the washin/washout of microvesicles in the kidney of a rat following administration of microvesicle preparations (randomised injection).

A quantitative analysis of microvesicles perfusion was performed using a software developed in-house (Bracco Suisse SA, Geneva, Switzerland) designed to quantify contrast echo-power amplitude within areas of interest (AOI). Contrast enhancement in the AOI was expressed as relative echo-power values ($rms^2$), which are proportional to the number of microvesicles in the selected AOI. Based on $rms^2$ values, maximum intensity (Imax, up to 30 sec post-injection) and late phase enhancement (5 and 10 min after injection) in rat kidney were evaluated. Persistency of microvesicles was determined as normalized value in percentage of the ratio between $rms^2$ values measured at late phase (at 5 and 10 minutes) and the Imax value.

TABLE 11

Persistency of microvesicles in-vivo

| Fatty acid composition | Persistency (5 min) | Persistency (10 min) |
|---|---|---|
| 3aA1 | 21.3% | 12.5% |
| 1aA1 | 5.9% | 1.8% |

As inferable from the above results, microvesicles according to the invention (with a mixture of saturated and unsaturated fatty acids) show an increased persistency after 5 and 10 minutes from injection, with respect to microvesicles comprising the same molar amount of only the saturated fatty acid.

The invention claime is:

1. A suspension of gas-filled microvesicles in a physiologically acceptable liquid carrier, said microvesicles having a stabilizing envelope comprising a phospholipid, a saturated fatty acid and an usaturated fatty acid, wherein the molar ratio between the saturated and the unsaturated fatty acid is from 2.5:1 to 1:8.

2. A suspension according to claim 1 wherein said molar ratio is from 1.5:1 to 1:7.5.

3. A suspension according to claim 2 wherein said molar ratio is from 1:1.5 to 1:4.

4. A suspension according to claim 1 wherein the saturated or unsaturated fatty acid is a carboxylic acid comprising a $C_{10}$-$C_{28}$ aliphatic chain.

5. A suspension according to claim 4 wherein said saturated fatty is selected from capric (n-decanoic), lauric (n-dodecanoic), myristic (n-tetradecanoic), pahnitic (n-hexadecanoic), stearic (n-octadecanoic), arachidic (n-eicosanoic), behenic (n-docosanoic), n-tetracosanoic acid and mixtures thereof.

6. A suspension according to claim 4 wherein said unsaturated fatty acid is selected from decenoic, dodecenoic, tetradecenoic, hexadecenoic, hexadecadienoic, octadecenoic, octadecadienoic, octadecatrienoic, octadecatetraenoic, eicosenoic, eicosadienoic, eicosatrienoic, eicosatetraenoic, eicosapentaenoic, docosaenoic, docosadienoic, docosatrienoic, docosatetraenoic, docosapentaenoic, tetracosenoic acid and mixtures thereof.

7. A suspension according to claim 1 wherein the molar ratio between phospholipids and the mixture of saturated/unsaturated fatty acids in the suspension is from 3:7 to 4:1.

8. A suspension according to claim 7 wherein said phospholipid is selected from phosphatidylcholine, ethylphosphatidylcholine, phosphatidylglycerol, phosphatidic acid, phosphatidylethanolamine, phosphatidylserine, phosphatidylinositol, sphingomyelin and mixtures thereof.

9. A suspension according to claim 1 wherein said gas-filled microvesicles further comprise a targeting ligand and/or a therapeutic agent.

10. A suspension according to claim 1 wherein said gas comprises a fluorinated gas.

11. A sealed vial consisting of:
a) a pharmaceutical formulation comprising a phospholipid, a saturated fatty acid and an unsaturated fatty acid, wherein the molar ratio between saturated and unsaturated fatty acid is from 2.5:1 to 1:8; and
b) a biocompatible fluorinated gas; and c) optionally a lyophilizing agent.

12. A vial according to claim 11 wherein the molar ratio between saturated and unsaturated fatty acid is from 1.5:1 to 1:7.5.

13. A vial according to claim 12 wherein the molar ratio between saturated and unsaturated fatty acid is from 1:1.5 to 1:4.

14. A vial according to claim 11 wherein the saturated or unsaturated fatty acid is a carboxylic acid comprising a $C_{10}$-$C_{28}$ aliphatic chain.

15. A vial according to claim 14 wherein said saturated fatty acid is selected from capric (n-decanoic), lauric (n-dodecanoic), myristic (n-tetradecanoic), pahnitic (n-hexadecanoic), stearic (n-octadecanoic), arachidic (n-eicosanoic), behenic (n-docosanoic), n-tetracosanoic acid and mixtures thereof.

16. A vial according to claim 14 wherein said unsaturated fatty acid is selected from decenoic, dodecenoic, tetradecenoic, hexadecenoic, hexadecadienoic, octadecenoic, octadecadienoic, octadecatrienoic, octadecatetraenoic, eicosenoic, eicosadienoic, eicosatrienoic, eicosatetraenoic, eicosapentaenoic, docosaenoic, docosadienoic, docosatrienoic, docosatetraenoic, docosapentaenoic, tetracosenoic acid and mixtures thereof.

17. A vial according to claim 11 wherein the molar ratio between phospholipids and the mixture of saturated/unsaturated fatty acids in the formulation is from 3:7 to 4:1.

18. A vial according to claim 17 wherein said phospholipid is selected from phosphatidylcholine, ethylphosphatidylcholine, phosphatidylglycerol, phosphatidic acid, phosphatidylethanolamine, phosphatidylserine, phosphatidylinositol, sphingomyelin and mixtures thereof.

19. A vial according to claim 11 wherein said formulation is in a freeze-dried form.

20. A pharmaceutical kit for the preparation of a suspension of gas-filled microvesicles comprising a vial according to claim 11 and a container containing a physiologically acceptable aqueous carrier.

21. A method of diagnosis which comprises:
administering to a subject a diagnostically effective amount of a suspension according to claim 1; and
subjecting said subject to a suitable imaging technique.

22. The method according to claim 21 wherein said imaging technique is ultrasound imaging.

\* \* \* \* \*

UNITED STATES PATENT AND TRADEMARK OFFICE
CERTIFICATE OF CORRECTION

PATENT NO. : 10,010,630 B2
APPLICATION NO. : 14/653793
DATED : July 3, 2018
INVENTOR(S) : Lassus et al.

Page 1 of 1

It is certified that error appears in the above-identified patent and that said Letters Patent is hereby corrected as shown below:

In the Claims

Column 20, Claim 1, Line 21 "usaturated" should read –unsaturated–.

Column 20, Claim 5, Line 33 "pahnitic" should read –palmitic–.

Column 21, Claim 15, Line 9 "pahnitic" should read –palmitic–.

Signed and Sealed this
Ninth Day of April, 2019

Andrei Iancu
*Director of the United States Patent and Trademark Office*